United States Patent [19]

Hennige et al.

[11] Patent Number: 5,492,126
[45] Date of Patent: Feb. 20, 1996

[54] PROBE FOR MEDICAL IMAGING AND THERAPY USING ULTRASOUND

[75] Inventors: Carl W. Hennige, San Jose; Edward C. Driscoll, Jr., Portola Valley, both of Calif.

[73] Assignee: Focal Surgery, Milpitas, Calif.

[21] Appl. No.: 236,344

[22] Filed: May 2, 1994

[51] Int. Cl.$^6$ ............................................. A61B 8/00
[52] U.S. Cl. ..................... 128/660.03; 128/662.06
[58] Field of Search ............... 128/660.03, 662.05, 128/662.06; 601/4; 606/14–16

[56] References Cited

U.S. PATENT DOCUMENTS

| | | | |
|---|---|---|---|
| 4,327,738 | 5/1982 | Green et al. | 128/660 |
| 4,779,624 | 10/1988 | Yokoi | 128/660.03 X |
| 5,036,855 | 8/1991 | Fry et al. | 128/660.03 |
| 5,117,832 | 6/1992 | Sanghvi et al. | 128/662.03 |
| 5,201,731 | 4/1993 | Hakky | 606/15 |
| 5,207,672 | 4/1993 | Roth et al. | 128/660.03 X |
| 5,222,501 | 6/1993 | Ideker et al. | 128/660.03 |
| 5,295,484 | 3/1994 | Marcus et al. | 128/660.03 |

*Primary Examiner*—Francis Jaworski
*Attorney, Agent, or Firm*—Blakely, Sokoloff, Taylor & Zafman

[57] ABSTRACT

A probe for inspecting and treating an internal organ of a patient. The probe includes a tube having a proximal end and a distal end. The tube has a flexible portion near the distal end. A head is coupled to the flexible portion at the distal end of the tube. The head includes a HIFU transducer. The probe also includes a mechanism for positioning the probe responsive to manipulation by a user. The probe may optionally include a direct viewing mechanism for viewing the area adjacent to the head, a ultrasound system for generating ultrasound images of the area adjacent to the head, and a lighting mechanism for illuminating the area adjacent to the head. The probe may be employed as an endoscope for applying HIFU therapy to internal organs of a patient.

10 Claims, 4 Drawing Sheets

PROBE FOR MEDICAL IMAGING AND THERAPY USING ULTRASOUND

FIELD OF THE INVENTION

This invention relates to probes that are used in medical applications for examination and treatment of organs inside the body, and more specifically to probes that use high intensity focused ultrasound to destroy diseased tissue.

BACKGROUND OF THE INVENTION

An endoscope is a probe which generally consists of a flexible or rigid tube that allows viewing of the inside of the body. A physician or medical specialist inserts one end of the endoscope (distal end) through a natural orifice such as the anus or mouth into a natural cavity such as the gastrointestinal tract. The endoscope contains a mechanism for conducting light from a light source external to the body to illuminate the internal cavity. The end of the endoscope which is not inserted (proximal end) is connected to a source of light which is coupled to the light conducting mechanism by optical components such as lenses or mirrors. The endoscope further contains a second mechanism for conducting light from the inside of the internal cavity to a viewing mechanism. The viewing mechanism may consist of an optical device which may be directly coupled to the eye of the medical specialist, or it may be coupled to a camera such as a video camera for viewing on a video monitor. An endoscope thus allows a medical specialist to see the inside of the cavity and to diagnose disease, anomalies, and the like. However, it does not provide any mechanism for applying therapy.

Endoscopes have also been developed with an ultrasonic device built at the distal end, and coupled with appropriate electronics at the proximal end, to perform ultrasonic imaging of the surfaces underlying the wall of the cavity. A probe having both optical viewing and ultrasonic imaging capabilities is described in U.S. Pat. No. 4,327,738 to Green et al. (1982). These devices provide another way to evaluate the health state of the tissue or organs, yet they still do not allow applying therapy.

Similarly, laparoscopic probes are a variation on the concept of endoscopes. Laparoscopic probes are inserted into the body through a perforation made into the skin, to observe and manipulate internal tissue and organs. Laparoscopic probes also require visual guidance, using optical visualization systems similar to those used in endoscopes, although sometimes the illumination, vision and manipulation probes are separate and inserted through separate skin incisions. Some laparoscopic instruments have been developed that contain ultrasonic imaging devices built into the distal end, for imaging beneath the surface of the organs that are visible by an optical viewing mechanism. Because of the expanded access to the organ in question via ad-hoc perforations, laparoscopic devices are very suited for surgery of internal organs by the use of miniature scalpels that are controlled or manipulated from a position external to the body.

While the images obtained by illumination or ultrasound in the prior art endoscopes and laparoscopes have proved to be a valuable tool in medical diagnosis, they do not directly perform the treatment of the identified anomalies.

Recently, ultrasound technology has been developed for use in providing therapy. Therapeutic ultrasound relies on applying ultrasonic waves of such intensity that tissue is heated to very high temperatures by the waves. When the tissue is heated to 42–45 degrees centigrade for extended periods of time, some physiological changes in the cells occur. This form of therapy is called hyperthermia. When tissues are heated to 60 degrees or higher, some cells are destroyed. This form of therapy is called ablation. The technology that performs this ablation requires high intensity ultrasound obtained by sharply focusing the acoustic waves. This form of ultrasound is generally known as "high intensity focused ultrasound", or HIFU.

The use of HIFU to treat anomalies has been mainly used extracorporeally (i.e. from outside the body). However, some organs and tissue to be treated may be inaccessible to extracorporeal beams due to obstruction by bone, lung or other major organs that do not allow the passage of ultrasonic waves.

OBJECTS AND ADVANTAGES

It is advantageous to add the capability of High Intensity Focused Ultrasound therapy to laparoscopes to allow surgeons to treat internal anomalies with HIFU. Similarly, it is desirable to have endoscopes with the capability to reach, visualize and treat diseased tissue with HIFU. In general, it is desirable to have a probe of the kinds described with the additional capability of applying therapy using HIFU.

SUMMARY OF THE INVENTION

According to one aspect of the present invention, a probe for inspection and treatment of an internal organ of a patient is provided. The probe includes a tube having a distal end and a proximal end. The tube is flexible near the distal end. The probe further includes a head coupled to the distal end of the tube, where a HIFU transducer is contained. The HIFU transducer may be constituted of a single element, an annular array of elements, a linear array of elements, or a curved linear array of elements. The elements generate ultrasonic waves as a result of electrical impulses. Thus, the present invention presents the advantages of access provided by conventional probes, with the unique ability to treat tissue or organs with HIFU.

Optionally, the probe may also include a separate ultrasonic transducer for generating an ultrasonic image of organs adjacent to the probe's head. Finally, the probe includes a positioning mechanism for causing the flexible portion to bend in response to manipulation by a user. Optionally, the probe further includes a visualization mechanism to allow the user to view organs adjacent to the probe's head. Other variants of the probe may include separate channels to perform other functions such as to conduct water or medications to the distal end, to affect suction to extract liquid or tissue samples for biopsy, and the like.

According to another aspect of the invention, a method for treating an internal organ is provided. According to the method, a probe having a HIFU transducer is provided. The head of the probe is inserted into an orifice in the patient's body. The tube of the probe is inserted into the orifice of the patient. The head of the probe is thereby caused to project deeper into the patient.

A portion of the tube adjacent to the head is caused to bend. The steps of inserting the tube and causing the portion of the tube adjacent to the head to bend are repeated until the head is adjacent to the internal organ of interest. Once the probe is in position, the HIFU transducer is then energized to generate ultrasonic waves toward the organ.

The method may also include the steps of generating ultrasound images of an area adjacent to the head, and directing the insertion of the head and tube based on the ultrasound images. The method may include a step for generating light to illuminate an area adjacent to the head. Optionally, the method may also include providing a direct viewing mechanism to view the area adjacent to the head and directing the insertion of the head and tube based on feedback from the direct viewing mechanism. A liquid such as saline solution or other solutions of medicinal nature may be injected through the probe. Also, samples of liquids or tissue may be suctioned out of the patient through the probe for further analysis.

BRIEF DESCRIPTION OF THE DRAWINGS

The invention may best be understood by referring to the following description and accompanying drawings which illustrate the invention. In the drawings.

DETAILED DESCRIPTION OF THE PREFERRED EMBODIMENT

Various embodiments of the present invention are directed towards a probe, such as those employed in endoscopy or laparoscopy, with the capability to apply High Intensity Focused Ultrasound. In the following description, numerous specific details are set forth, such as types of transducers, etc., in order to provide a thorough understanding of the present invention. It is understood, however, that these specific details are not required to practice the present invention. In other instances, well-known components have not been described in detail in order to not unnecessarily obscure the present invention.

Figure 1:
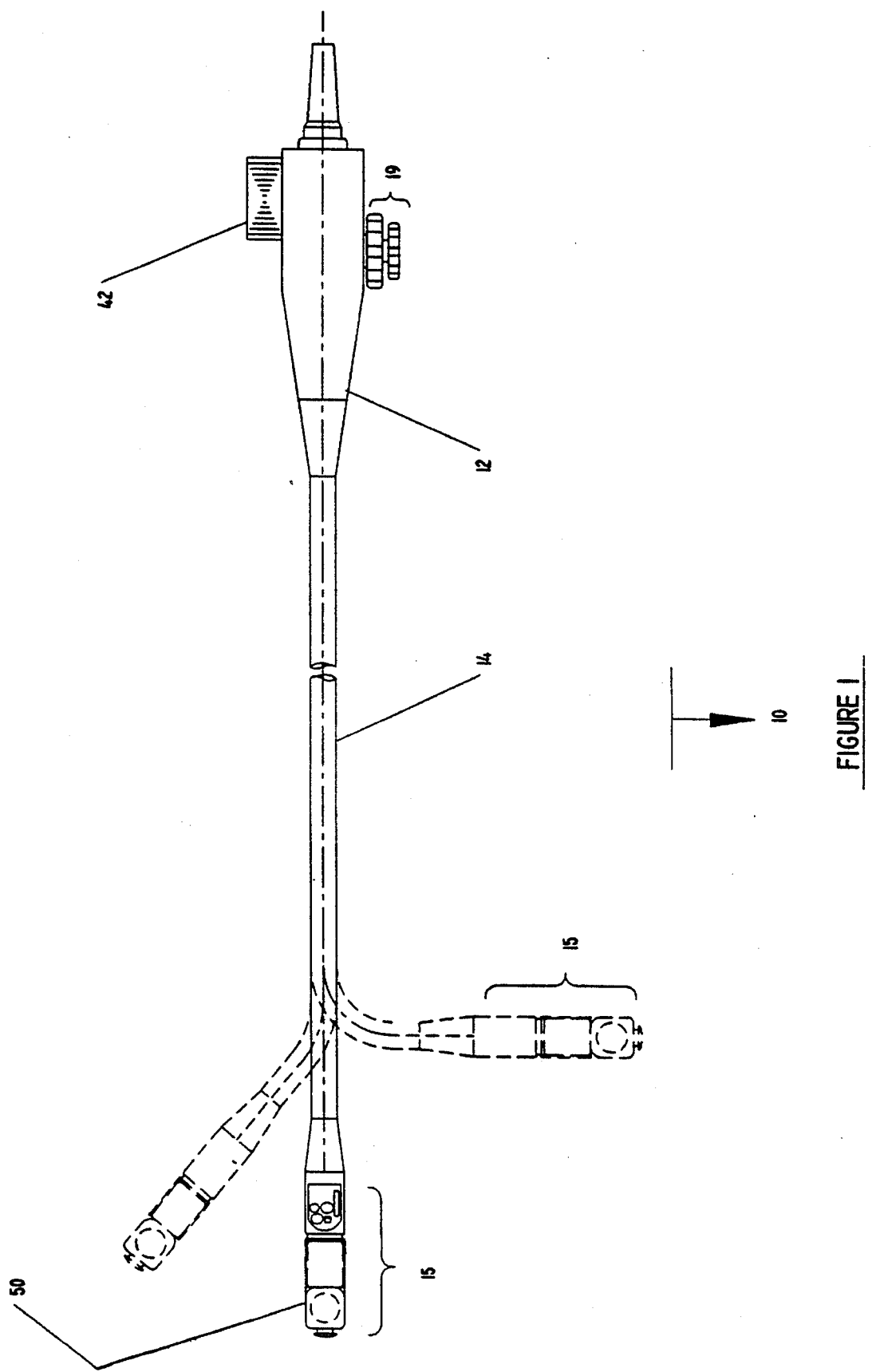
FIG. 1 is an elevational view of a probe according to an embodiment of the present invention.

Referring to FIG. 1, the probe is shown according to the presently preferred embodiment of the invention. Probe 10 is connected to a housing 12 through a tube 14. The end of probe 10 opposite housing 12 has a head 15. A portion of tube 14 adjacent to head 15 is flexible. Transducer 50 is attached to head 15 such that transducer 50 faces away from tube 14 in a direction substantially perpendicular to the axis of head 15.

While probe 10 is described here with a flexible tube and a transducer facing a direction perpendicular to the axis of head 15, probe 10 may alternately employ a rigid tube and a transducer facing at various angles relative to the axis of head 15. The specific tube type and transducer orientation will vary based on the specific application of the invention.

A flexure control mechanism, such as those found in endoscopes made by Olympus, Pentax, Stortz, ACMI, etc. is employed to control bending of tube 14 adjacent to head 15. Preferably, probe 10 has a flexure control mechanism which includes a control handle 19 operatively connected to head 15 through tube 14. By operating control handle 19, a user causes the distal end of tube 14 to flex, providing probe head 15 with four quadrant movement.

Figure 2:
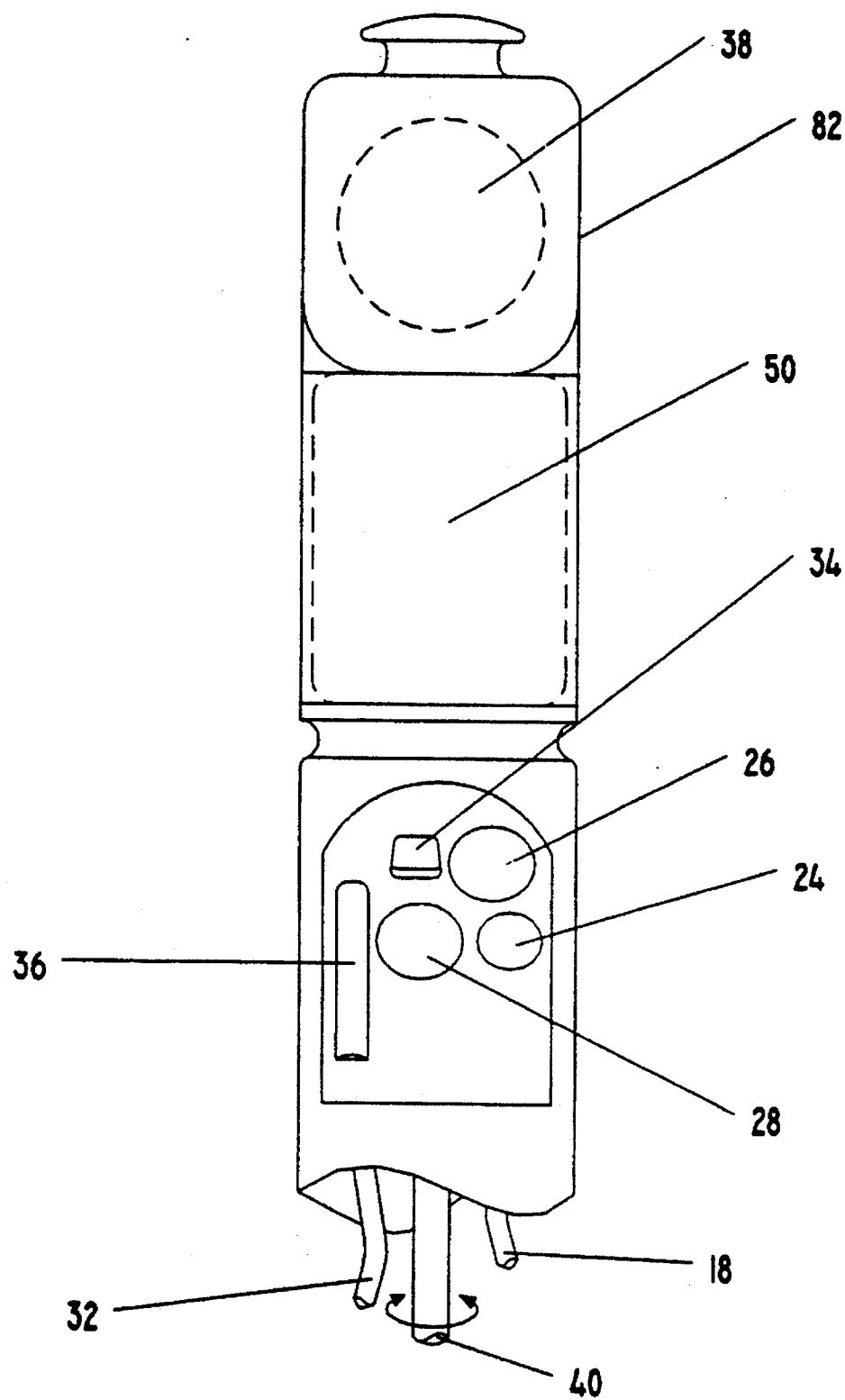
FIG. 2 is a detail of the probe head, in frontal view, which includes a HIFU transducer.

Referring to FIG. 2, tube 14 contains a light-transmitting fiber bundle 18, which extends axially through tube 14 and head 15, and terminates at windows 24 and 26 near the middle of head 15. The fiber-optic bundle 18 passes through tube 14 into housing 12. A suitable source of illumination not shown can be applied at housing 12 to provide illumination at windows 24,26. Probe 10 also houses an optical viewing system, including an objective lens 28. Lens 28 is attached to the end of an image guide bundle 32 of light-transmitting fibers. The bundle 32 passes through tube 14 to control housing 12. Bundle 32 may be suitably coupled to a video camera (not shown) at the eyepiece 42 in the head 15 to record or visually display the objects within view of the objective lens 28. Although this visualization is advantageous, it is not necessary for the invention to perform its function, as any mechanism which provides positioning feedback—such as ultrasound—may be used.

Figure 3:
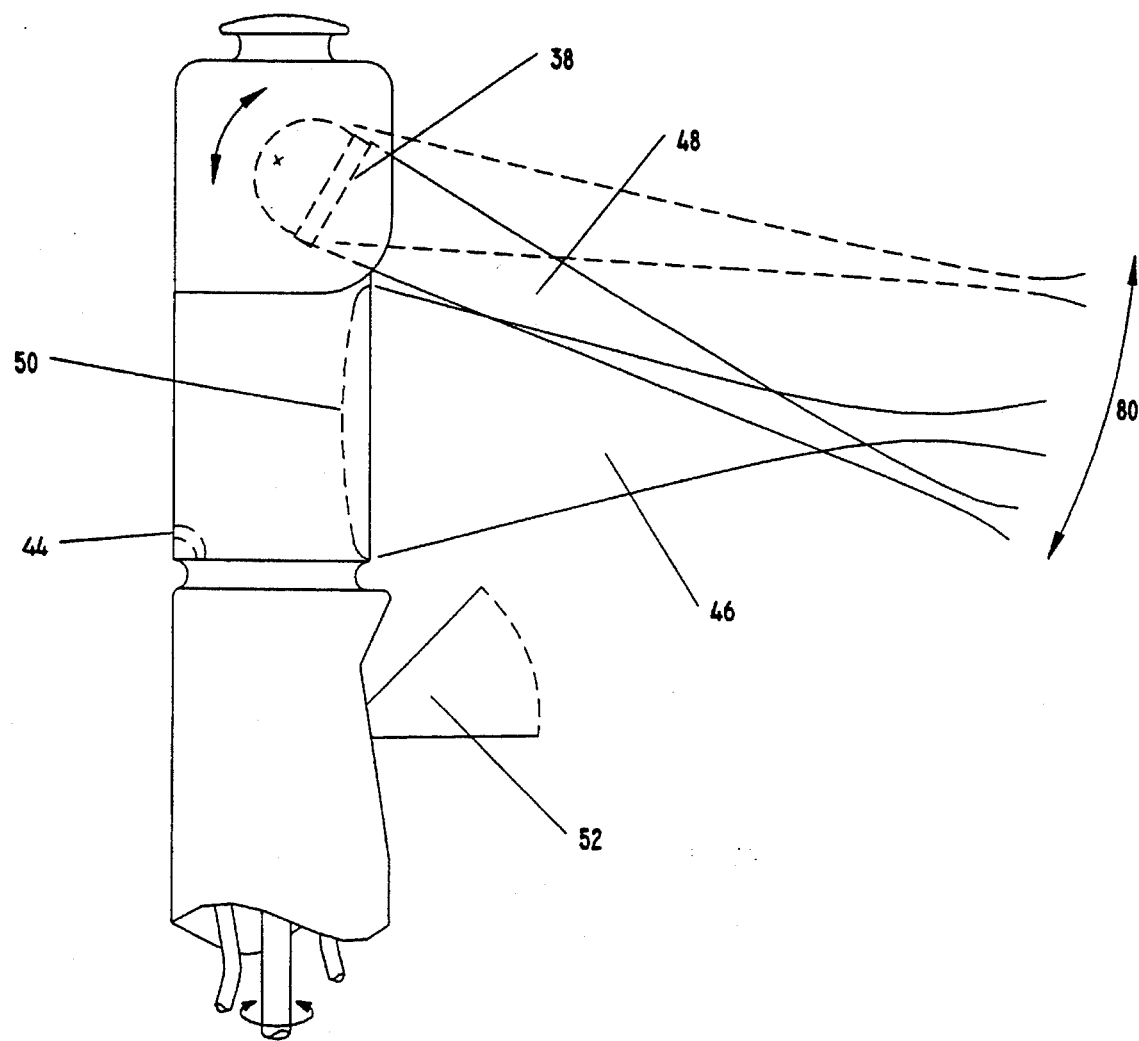
FIG. 3 is a detail of the probe head, in lateral view, which includes a HIFU transducer.

The head 15 also comprises a nozzle 34 near the windows 24 and 26 and lens 28 to inject water for cleaning of the lens 28 and windows 24 and 26. The same nozzle 34 can be used to deliver medicated solutions to the neighborhood of the head 15. Separate nozzle 44 (shown in FIG. 3) is used to inject water when a sheath is employed to separate the probe from the patient; the water is used to inflate the sheath and assist in positioning the head 15 close or away from the organ of interest. Head 15 also includes an outlet 36 from which a variety of devices can be controlled from housing 12, such as forceps or a biopsy needle, to extract tissue samples. Head 15 also comprises an ultrasonic imaging transducer 38 which pivots within head 15, controlled by a rotating shaft 40 to provide ultrasonic imaging by scanning, using a wobbling motion. As a result of the wobbling motion, the beam describes a plane surface, as shown in FIG. 3. FIG. 3 also shows imaging ultrasonic beam 48, which upon wobbling intercepts the focal zone of therapeutic ultrasonic beam 46. For reference, the approximate field of view of the optical objective lens 28 is shown as 52. The wobbling transducer could be replaced by a spinning transducer, such as that found in the Olympus endoscope, modified by tilting the transducer axis—but not its axis of rotation—in order to intercept the focal zone of the therapeutic beam.

The present invention is not limited to using a therapy transducer 50 having a radiating surface which conforms generally in shape to that shown in FIG. 2. The transducer 50 may be an annular array, a linear array, or another transducer configuration. Thus, the therapy transducer 50 of the present invention may be a transducer having a variable focal depth. Similarly, the imaging transducer 38 can be replaced with an annular array, a phased array, a convex array, or other configuration suitable for imaging in the region near the head 15.

It should be noted that transducer 50 is preferably smaller in size than prior art HIFU transducers. However, transducer 50 is able to generate an ultrasonic beam of sufficient strength to provide effective treatment. Even though a variety of transducers may be used, steps may have to be taken in their construction to ensure their proper functioning. In general, transducers for HIFU require that they operate at higher temperatures (typically 50 to 70 degrees centigrade) than those encountered in transducers for pulsed mode operation, such as imaging or Doppler ultrasonic transducers. Due to mechanisms intrinsic to the piezoelectric materials used for their construction, some inefficiency exists in the ability of the transducers to convert the electrical energy into acoustic energy, resulting in heating of the device. As a consequence of this heating, and given the small size of the HIFU transducer, steps must be taken during its construction to allow it to operate even at these higher temperatures, without loss in efficiency or physical integrity. One technique for designing efficient transducers is the use of matching layers between the piezoelectric material and the coupling medium (water or tissue). If a matching layer is used to improve efficiency, it must be built of some material that will not degrade with heat. Transducers having suitable compositions of piezoelectric ceramic and matching layer can be obtained from Etalon, Inc. (Lizton, Ind.). The specific transducer used in this embodiment is a section of a sphere 2.5 cm in radius of curvature, showing a rectangular face 13 mm by 20 mm. Additionally, water may be used to refrigerate the transducer 50 to cool transducer 50.

Operation

Figure 4:
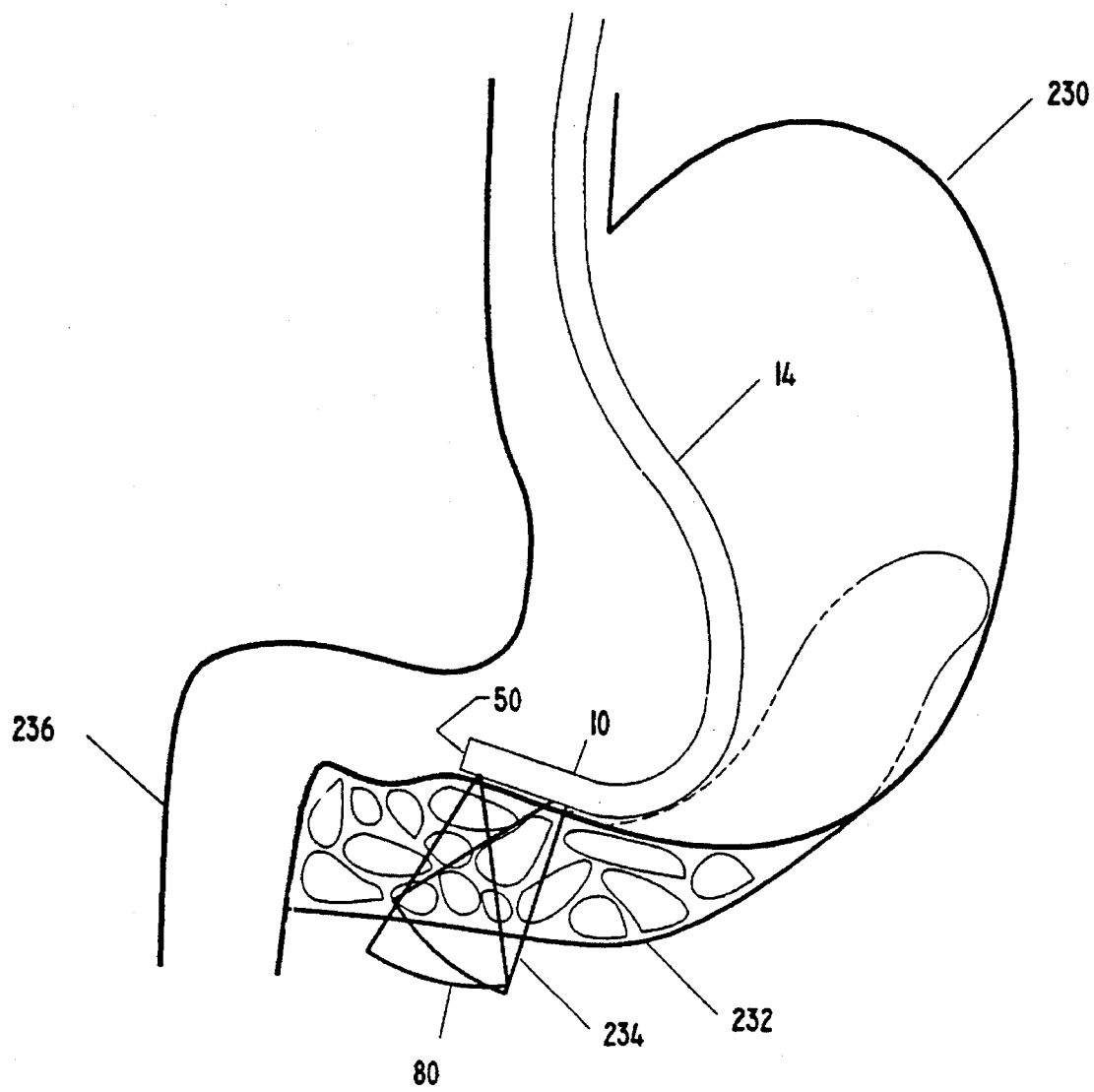
FIG. 4 illustrates a sectional view of the transducer illustrated in FIG. 1, applied to view and treat a portion of the pancreas of a patient.

For purposes of illustration, and not by way of limitation, the present apparatus is shown, in FIG. 4, employed in the gastrointestinal system of a patient. The detection of malignancy outside the tubular gastrointestinal tract is difficult, and the diagnosis of cancer involving the pancreas and pancreatic head, peritoneal cavity and mesentery is particularly difficult. However, the proximity of the pancreas to the stomach and duodenum make it and its surrounding structures ideal for high-resolution ultrasonic visualization and therapy with the ultrasonic probe of the present invention.

FIG. 4 shows the probe 10 as inserted into the patient's stomach 230. Conventional optical guidance mechanisms may be used to guide the probe through the esophagus and into desired placement within the gastrointestinal tract. Many endoscopists prefer using the eyepiece 42 when guiding the probe into the desired position, and others prefer attaching a video camera to eyepiece 42 for display of the image on a video monitor. Using eyepiece 42, the ultrasonic probe head 15 is guided into desired position for ultrasonic treatment of underlying soft tissue. In FIG. 4, the probe 10 is shown advanced to the greater curvature of the stomach 230 adjacent the pancreas 232. Through manipulation of the probe, firm contact of the cylindrical lens 82 of the imaging transducer and HIFU transducer 50 with the mucosa is effected, enabling ultrasonic scanning and/or therapy to proceed. At this time, the eyepiece 42 may be removed from the housing 12 and replaced by a camera for connection of the optical system to a closed circuit television that displays the optical image on a video monitor. Both the optical image and ultrasonic image can be simultaneously displayed, and viewable, by the operator. In FIG. 4 the ultrasonic imaging surface 80 is identified, together with the optical viewing angle 234. By proper manipulation of the probe 10, ultrasonic scanning and therapy of the pancreas may be provided from the tail area thereof to the pancreatic head through the stomach wall. By maneuvering the probe into the duodenum 236, additional ultrasonic imaging on the head of the pancreas 232 from different locations is possible. High resolution ultrasonic images which extend from a position close to the surface of the probe to a depth of approximately 4 cm are possible.

As is evident by the foregoing, probe 10 allows an operator to position a HIFU transducer adjacent to organs in the body which require treatment. Thus, ultrasound beam therapy can be used to treat organs which are otherwise inaccessible due to obstruction by bone, lung or other major organs.

Probe 10 embodies fiber optics for direct visualization. Probe 10 may also contain fluid lines for filling and flushing cavities. It is often advantageous to supply fluid through such lines to fill or evacuate cavities to remove air. The fluid lines may also supply fluid to flush cavities for better visualization, or to inflate or deflate a sheath for positioning the probe head. Optionally, the fiber-optics and fluid lines can be combined, as is commonly known in the art.

By the incorporation of a HIFU transducer 50 on the head 15 of probe 10, the HIFU transducer 50 is allowed to enter human body openings. A user can position transducer 50 adjacent to an organ which requires treatment by manipulating the handle 19 based on visual feedback supplied by fiber-optic direct visualization, ultrasound imaging, or both. Once positioned, HIFU transducer 50 can be activated to perform therapy on the target organ. In some instances, ultrasound therapy performed as described above may be the only viable therapy for several types of inoperable cancer tumors. Probe 10 further provides physicians and researchers with the opportunity to explore other regions of the body for possible ultrasound therapy applications.

Ramifications and Scope

While a specific embodiment of the present invention has been described, various modifications and substitutions will, by this disclosure, no-doubt become apparent to one skilled in the art. Such modifications and substitutions are within the scope of the present invention, and are intended to be covered by the following claims.

What is claimed is:

1. A probe for inspecting and treating an internal organ of a patient, the probe comprising:
   a tube having a proximal end and a distal end, the tube having a flexible portion near the distal end;
   a head coupled to the flexible portion at the distal end of the tube;
   an ultrasonic image generation unit disposed within the head, the ultrasonic image generation unit being configured to generate a first set of ultrasonic waves for generating images of tissue in a first zone;
   a HIFU generating unit disposed within the head, the HIFU generating unit being configured to generate a second set of ultrasonic waves for treating tissue in a second zone;
   a positioning mechanism for causing the flexible portion to bend responsive to manipulation by a user; and
   wherein at least one set of said first and second sets of ultrasonic waves are generated at an angle relative to said head to cause said first zone to intersect with said second zone.

2. The probe of claim 1 further comprising optical visualization mechanism for allowing the user to view tissue adjacent to the probe's head.

3. The probe of claim 2, further comprising cooling means for water cooling the HIFU generation unit.

4. The probe of claim 1 wherein the HIFU generating unit is configured to transmit and receive waves to generate an ultrasonic image and to transmit ultrasonic waves for therapy.

5. The probe of claim 1 wherein said ultrasonic image generation unit has a variable orientation relative to said head, the probe further comprising a mechanism for changing said variable orientation to affect the angle, relative to said head, at which said first set of ultrasonic waves is generated.

6. A method for treating an internal organ, the method comprising the steps of:

a) providing a probe having a tube having a first end and a second end, a HIFU generation unit and an ultrasonic image generation unit being supported in a head connected to said first end;

b) inserting the head of the probe into an orifice of a patient;

c) inserting the tube of the probe into the orifice of the patient, thereby causing the head of the probe to project deeper into the patient;

d) causing a portion of the tube adjacent to the head to bend;

e) repeating steps (c) and (d) until the head is adjacent to the internal organ; and f) energizing the HIFU generation unit to generate a first set of ultrasonic waves toward a first zone on the organ;

g) energizing the ultrasonic image generation unit to generate a second set of ultrasonic waves toward said first zone on said organ while said HIFU generation unit is generating said first set of ultrasonic waves;

h) generating an image of said first zone based on said second set of ultrasonic waves.

7. The method of claim 6 further comprising the steps of:

generating fight to illuminate an area adjacent to the head;

providing a direct viewing mechanism to view the area adjacent to the head; and directing the insertion of the head and tube based on feedback from the direct viewing mechanism.

8. The method of claim 7 further comprising the steps of:

generating ultrasound images of an area adjacent to the head;

directing the insertion of the head and tube based on the ultrasound images; and directing the application of therapy based on feedback from the ultrasound images.

9. The method of claim 8 wherein the step of generating ultrasound images is performed based on signals from the HIFU generation unit.

10. The method of claim 6 further comprising the step of altering the orientation of said ultrasonic image generation unit from a first orientation in which said second set of ultrasonic waves are not directed toward said first zone to a second orientation in which said second set of ultrasonic waves are directed toward said first zone.

* * * * *